US012411357B2

(12) United States Patent
Jones

(10) Patent No.: US 12,411,357 B2
(45) Date of Patent: Sep. 9, 2025

(54) ADJUSTABLE EYEWEAR RESTRAINTS, SYSTEMS, AND METHODS

(71) Applicant: Alpine Innovations LLC, Lehi, UT (US)

(72) Inventor: Darren Jones, American Fork, UT (US)

(73) Assignee: Alpine Innovations LLC, Lehi, UT (US)

( * ) Notice: Subject to any disclaimer, the term of this patent is extended or adjusted under 35 U.S.C. 154(b) by 0 days.

(21) Appl. No.: 18/369,102

(22) Filed: Sep. 15, 2023

(65) Prior Publication Data

US 2024/0085722 A1 Mar. 14, 2024

Related U.S. Application Data

(63) Continuation of application No. 17/157,937, filed on Jan. 25, 2021, now abandoned, which is a
(Continued)

(51) Int. Cl.
*G02C 3/00* (2006.01)
*A61F 9/02* (2006.01)
*A63B 33/00* (2006.01)

(52) U.S. Cl.
CPC .............. *G02C 3/003* (2013.01); *A61F 9/027* (2013.01); *A63B 33/002* (2013.01); *G02C 3/006* (2013.01); *G02C 2200/20* (2013.01)

(58) Field of Classification Search
CPC . G02C 3/00; G02C 3/003; G02C 3/02; G02C 3/006; G02C 5/14; G02C 5/22;
(Continued)

(56) References Cited

U.S. PATENT DOCUMENTS 4,391,498 A * 7/1983 Rengstorff ........... G02C 5/2209
351/111
7,467,867 B1 * 12/2008 Williams ............... G02C 3/006
D16/339
(Continued)

FOREIGN PATENT DOCUMENTS

FR 2854471 A1 * 11/2004 ............. G02C 3/003

OTHER PUBLICATIONS

English translation of FR-2854471. (Year: 2004).*

*Primary Examiner* — Jie Lei
(74) *Attorney, Agent, or Firm* — Thorpe North & Western, LLP; David W. Osborne

(57) ABSTRACT

An adjustable eyewear restraint comprises a first strap having a first adjustment end and a first eyewear coupling end, and a second strap having a second adjustment end and a second eyewear coupling end. The straps are slidably and frictionally engageable to one another to allow adjustment of a length of the restraint by moving adjustment ends of the straps relative to each other. The straps can be slidably interwoven to each other about opening(s) of respective adjustment ends. The opening(s) slidably receive an opposing strap. A strap has a loop, coupleable to eyewear, that comprises first and second edges attached together to form an attachment portion substantially in-line with the first edge. A frictional element is frictionally and slidably coupleable to an earpiece to retain the loop and allow adjustment of a length of an eyewear retainer. Associated systems and methods are provided.

12 Claims, 9 Drawing Sheets

Related U.S. Application Data continuation of application No. 16/579,728, filed on Sep. 23, 2019, now abandoned, which is a continuation of application No. 15/287,645, filed on Oct. 6, 2016, now abandoned.

(60) Provisional application No. 62/237,970, filed on Oct. 6, 2015.

(58) Field of Classification Search
CPC ........ G02C 2200/20; A61F 9/027; A61F 9/02; A63B 33/002; A63B 33/00
USPC ... 351/154–158, 41, 43, 111, 121, 123, 142; 2/13, 421, 426, 444, 448, 452
See application file for complete search history.

(56) References Cited

U.S. PATENT DOCUMENTS

| | | | |
|---|---|---|---|
| 7,845,795 B2 * | 12/2010 | Williams | G02C 3/003 2/452 |
| D669,115 S * | 10/2012 | Kalbach | D16/339 |

* cited by examiner

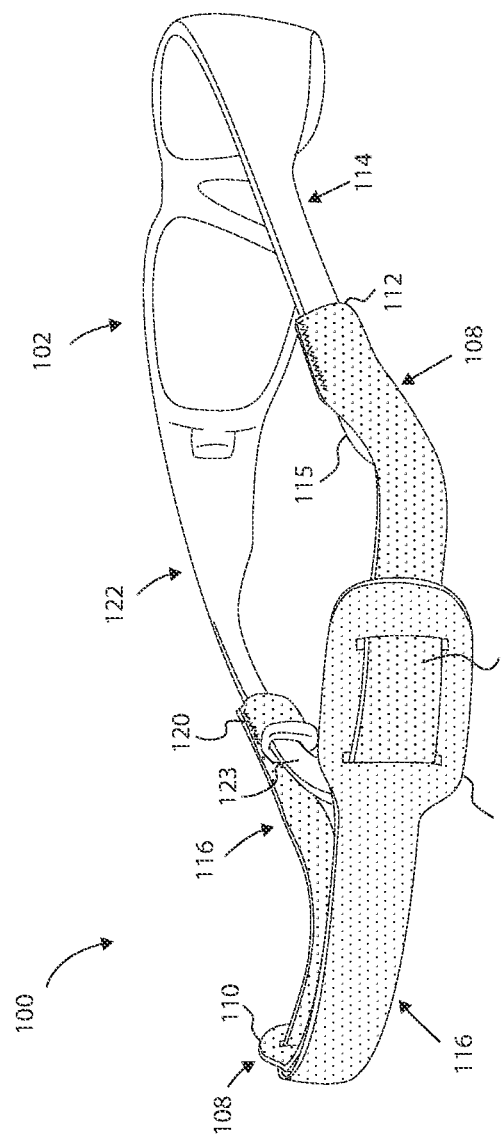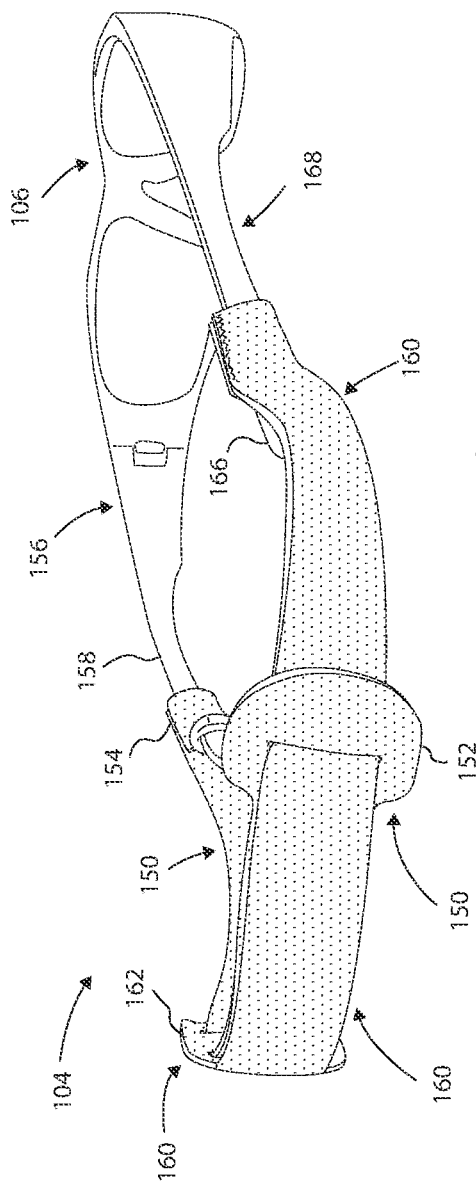

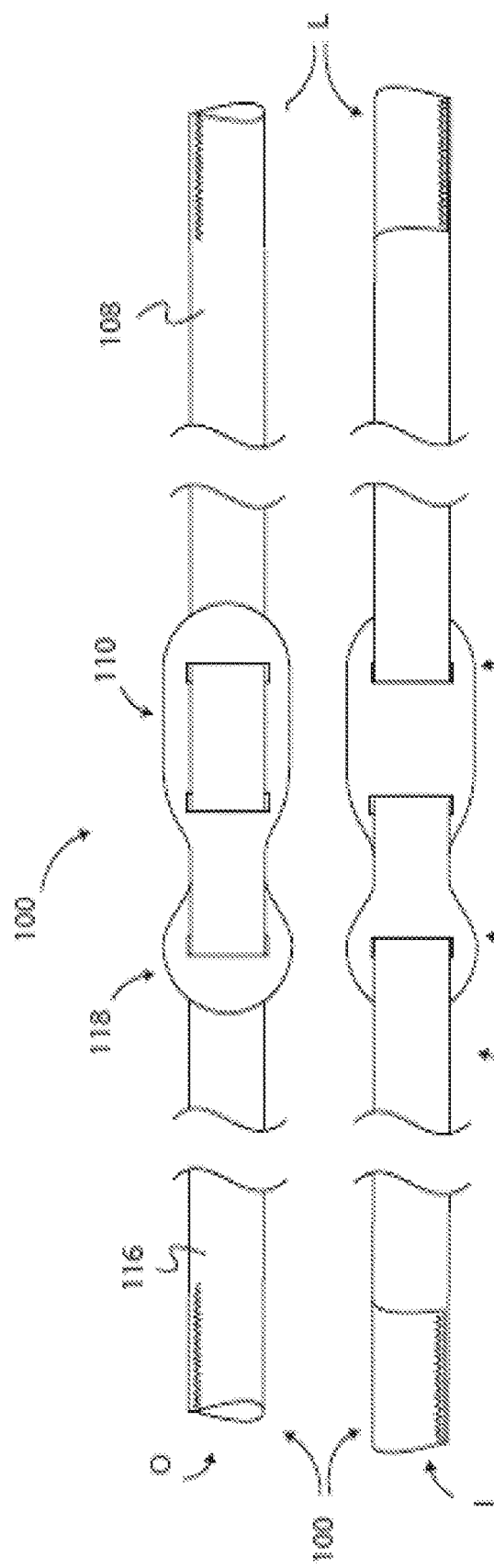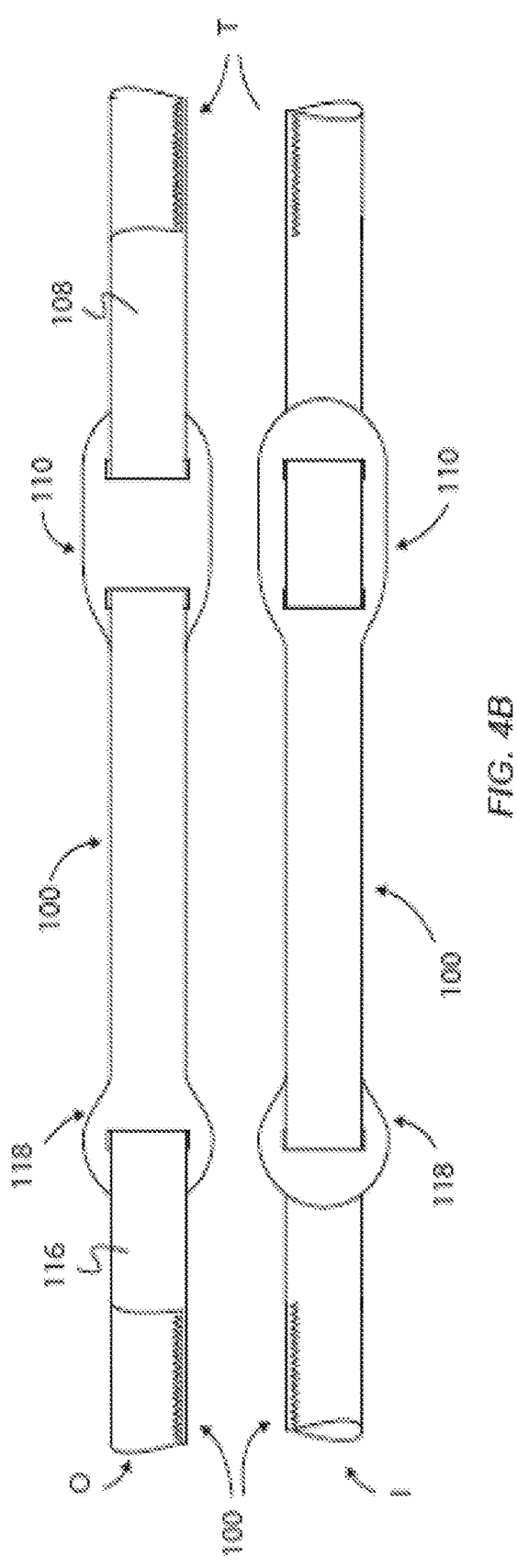

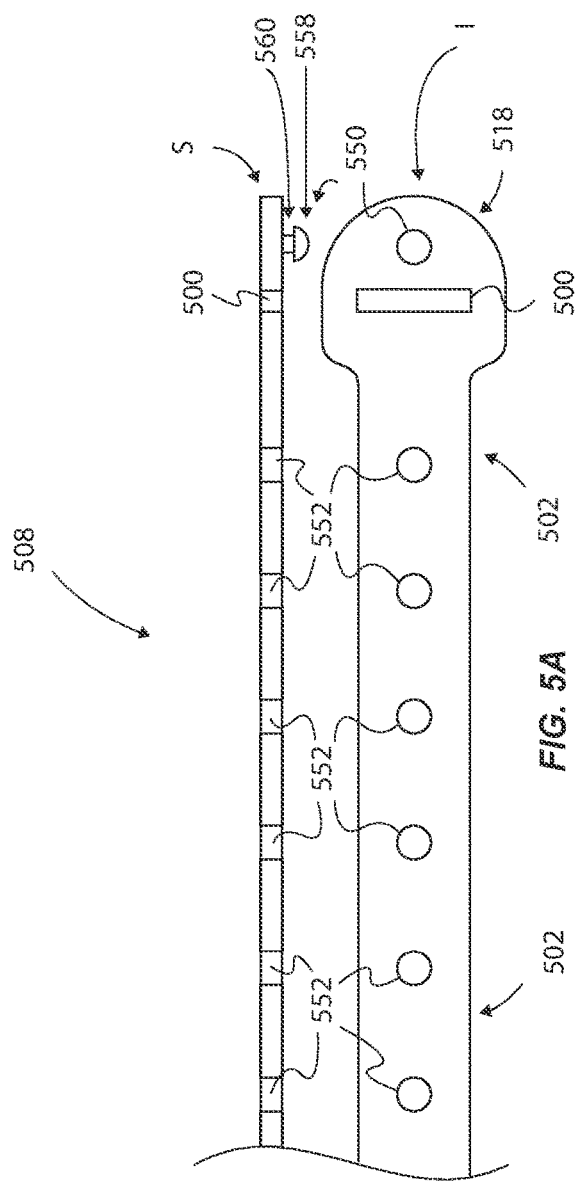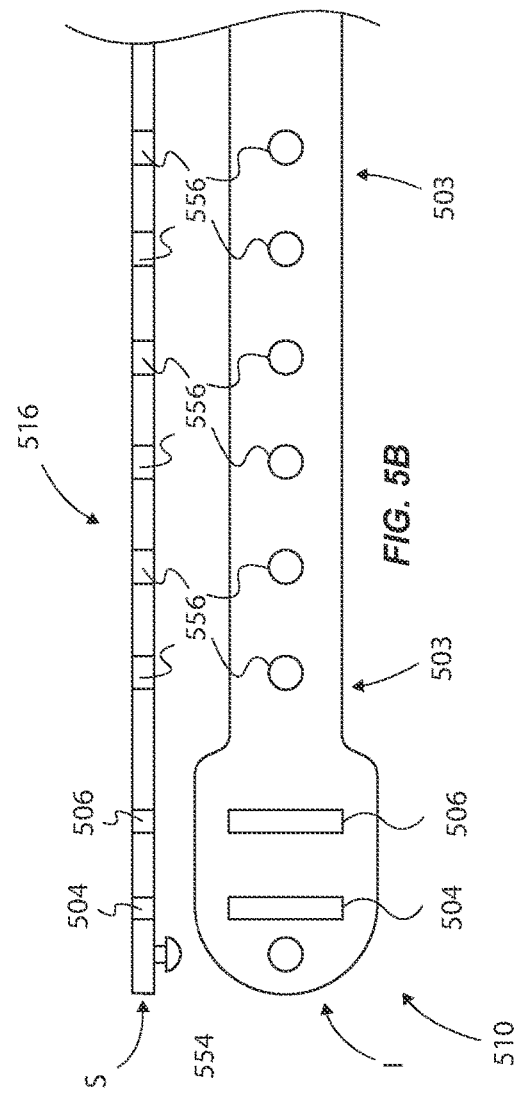
FIG. 5A
FIG. 5B

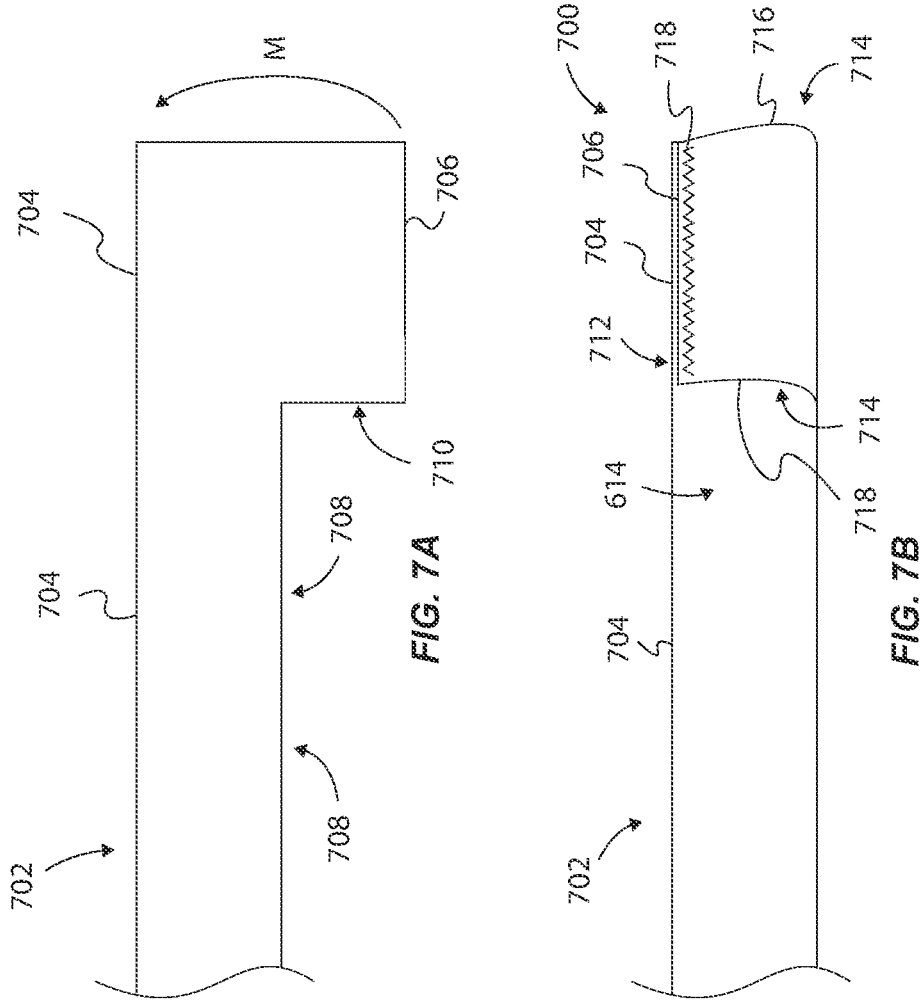

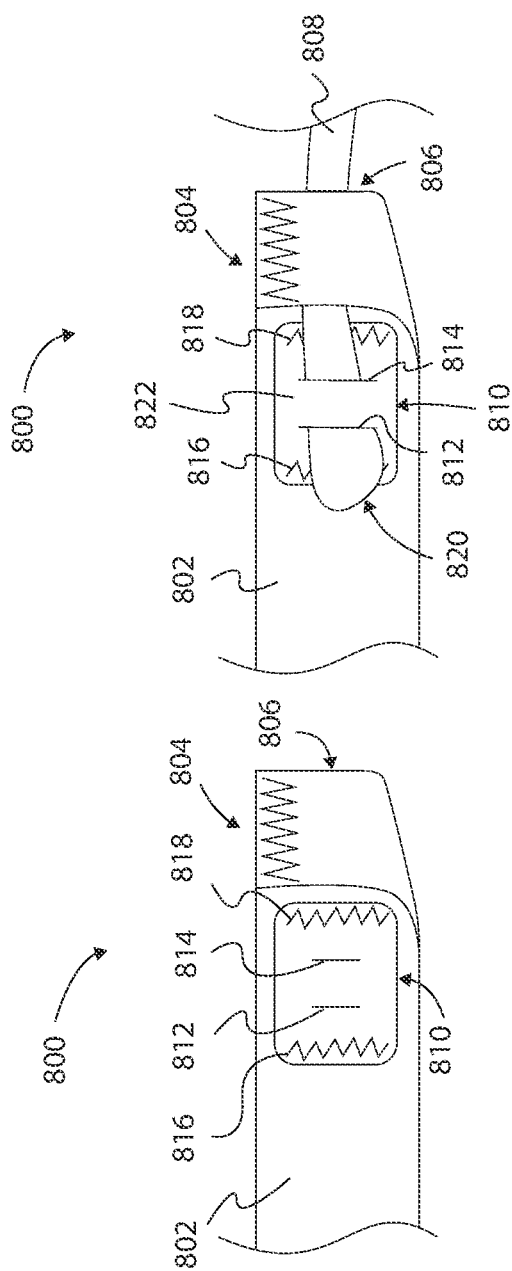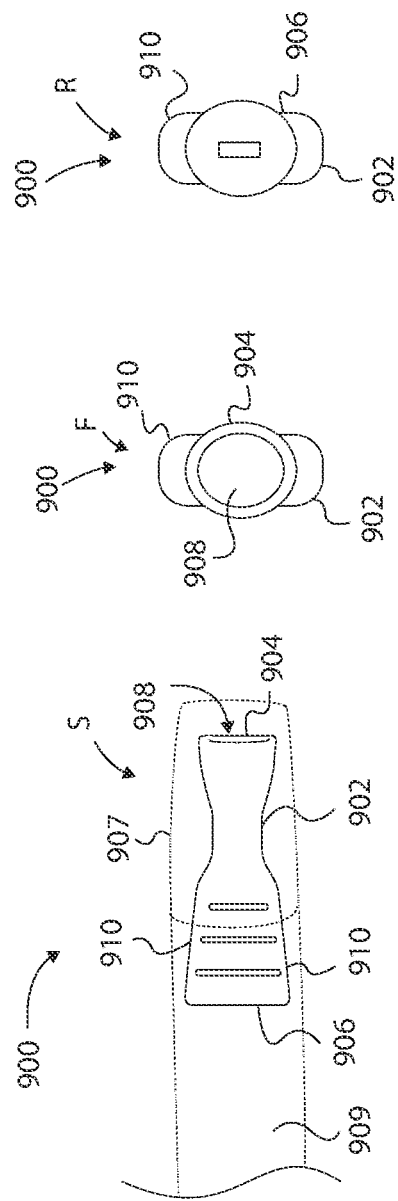

ADJUSTABLE EYEWEAR RESTRAINTS, SYSTEMS, AND METHODS

PRIORITY DATA

This application is a continuation of U.S. patent application Ser. No. 17/157,937, filed Jan. 25, 2021, which is a continuation of U.S. patent application Ser. No. 16/579,728, filed Sep. 23, 2019, which is a continuation of U.S. patent application Ser. No. 15/287,645, filed Oct. 6, 2016, which claims the benefit of U.S. Provisional Patent Application Ser. No. 62/237,970, filed on Oct. 6, 2015, each of which are incorporated herein by reference.

BACKGROUND

Eyewear can have a tendency to become misaligned or maladjusted on a user, rendering the eyewear less effective or inoperable. Even worse, during rigorous physical activities, such as playing a sport, eyewear can be knocked or otherwise thrown from a user's face. Yet other environments, such a laboratories or workshops may require the frequent donning and removal of eyewear. In such circumstances as well as others, it may simply be convenient for a user to have a designated place close at hand to keep the eyewear for ready use.

Accordingly, a variety of fastening mechanisms, straps, lanyards, and the like have been used to secure eyewear about a user, including in an operable and desirable position. Many of such fasteners are of a single fixed length and merely prevent the eyewear from falling to the ground by anchoring the eyewear to a user's neck. Where the fastener is adapted to secure the eyewear in an operable position (i.e. on a user's face), most often it is difficult or impossible to simply and easily move the eyewear to a non-operable position without completely disassociating the eyewear from the user. This is often due to the difficulty of the mechanism provided of tightening and loosening the fastener.

SUMMARY

Accordingly, the present inventor has identified a need for eyewear fasteners that are capable of both securing the eyewear in an operable position and are simple and easy to adjust in order to allow the eyewear to be easily moved from the operable position to a non-operable position in some embodiments without effectively untethering the eyewear from the user. Adjustable eyewear restraints, and associated methods, are described herein that can both secure the eyewear and be easily adjustable to allow the eyewear to be moved and adjusted in length as desired by a wearer.

In one example there is provided an adjustable eyewear restraint, comprising a first strap comprising a first adjustment end and a first eyewear-coupling end, with said first eyewear coupling end being coupleable to a first eyewear frame portion. A second strap comprises a second adjustment end and a second eyewear-coupling end, with said second eyewear coupling end being coupleable to a second eyewear frame portion. Thus, said first strap and said second strap being slidably engageable to one another to allow adjustment of a length of the restraint by moving at least one of the first adjustment end and the second adjustment end relative to the other one. In some examples, the first adjustment end of the first strap includes a first opening slidably frictionally engageable to the second strap, and the second adjustment end of the second strap includes a second opening and a third opening. Each of the second and third openings can be slidably frictionally engageable to the first strap. Each opening can be sized and shaped to provide sufficient frictional force, between the opening and the respective strap slidably engageable there through, to retain the straps to each other about a wearer's head. In some examples, each opening has a cross sectional area smaller than a cross section area of the respective strap slidably engageable through the respective opening. In some examples, each adjustment end comprises a pull tab positioned on the same side of the retainer when the straps are slidably engaged to each other. In some examples, the straps are slidably engaged to each other such that a length of the retainer is shortened when the adjustment ends are pulled away from each other, and such that a length of the retainer is lengthened when the adjustment ends are pulled toward each other. The straps can be slidably interwoven to each other about respective adjustment ends to form a substantially planar retainer configuration. In some examples, each opening comprises at least one of an aperture, a slot, or a loop.

In one example, the first strap comprises a first male attachment and a first plurality of female attachments, and the second strap comprises a second male attachment and a second plurality of female attachments. The first plurality of female attachments is selectively interlockable to the second male attachment, and the second plurality of second female attachments is selectively interlockable to the first male attachment component.

In one example, each strap comprises a first edge and an opposing second edge attached together, proximate respective eyewear coupling ends, to form a loop that receives a respective earpiece. The edges are attached to form an attachment portion substantially in-line with the first edge. In one example, the first edge comprises an upper edge extending along a length of the strap, and the second edge comprises a lower edge opposite the upper edge. In one example, the second edge has a length shorter than a length of the first edge. In one example, the attachment portion secures the first edge to the second edge by at least one of stitches, adhesive, fasteners, liquid plastic, and combinations thereof. In one example, the attachment portion comprises a predetermined length that is approximately a length of the second edge. In one example, the predetermined length is between approximately ⅛ inch and ¾ inch. In one example, said loop is sized and shaped to frictionally receive and retain the earpiece. In one example, said loop is sized and shaped to loosely receive the earpiece, wherein an external frictional element is required to retain the earpiece within the loop.

In one example there is provided an eyewear restraint system comprising a strap having an eyewear-coupling end slidably coupleable to an earpiece. The eyewear-coupling end can have a loop sized and shaped to allow a portion of the earpiece to pass through the loop. A frictional element is coupleable to the earpiece and positionable adjacent the loop of the strap, with said frictional element having a size and shape sufficient to frictionally engage the earpiece and retain the earpiece through the loop. In some examples, the frictional element has a perimeter body portion that defines a cross sectional area larger than a cross sectional area of an aperture of the loop. In some examples, the frictional element comprises an O-ring, or other device with an aperture, (e.g. a wedge shaped device) comprised of a compliant material and having an aperture sized and shaped to receive the earpiece such that the frictional element is frictionally and slidably coupleable to the earpiece for adjustment of the eyewear coupling end.

In one example, the frictional element comprises an earpiece retainer having a first end and a second end. The first end is positioned through the loop and having an opening sized and shaped to removably attach the earpiece retainer to the earpiece, and the second end is positioned at least partially within the loop and having an enlarged interfacing portion that frictionally couples the earpiece retainer within the loop.

In one example, the frictional element comprises a panel attached to the strap adjacent the loop, the friction panel having at least one opening configured to retain the earpiece.

In one example there is provided an adjustable eyewear restraint system comprising a pair of eyewear having a first earpiece and a second earpiece. A first adjustable eyewear restraint comprises a pair of straps, each strap having a loop slidably coupled to a respective earpiece of the pair of eyewear. The pair of straps are slidably and frictionally engaged to one another to allow adjustment of a length of the first adjustable eyewear restraint by moving at least one of the straps relative to the other strap. A second adjustable eyewear restraint comprises a pair of frictional elements. Each frictional element is slidably and frictionally coupled to a respective earpiece to allow adjustment of a length of the first adjustable eyewear restraint by moving at least one of the frictional elements relative to the respective earpiece. In some examples, each strap comprises an inner planar surface facing the pair of eyewear and an outer planar surface positioned opposite the inner planar surface. Each strap comprises a pull tab positioned adjacent the outer planar surface of a respective straps such that the pull tabs are graspable proximate the outer planar surface of each strap.

In some examples, the straps are comprised of a positively buoyant material having a selected volume and density sufficient to impart positive buoyancy on the pair of eyewear when the straps and eyewear are in fresh or salt water. The positively buoyant material can comprise a polymeric and/or fabric material (e.g. neoprene) material, and the pair of eyewear can weigh at least 30 grams.

In one example there is provided a method of adjusting a length of an eyewear restraint. The method can comprise pulling a first adjustment end of a first strap away from a second adjustment end of a second strap to shorten a length of the restraint and tighten an eyewear restraint about a wearer's head when coupled to a pair of eyewear. The first strap can be slidably and frictionally engaged to the second strap. The method can comprise pulling the first and second adjustment ends towards each other to lengthen a length of the restraint to loosening the restraint about the wearer's head. The method can comprise disposing a first earpiece of the pair of eyewear through a first loop of the first strap such that the first earpiece extends at least partially through the first loop. The method can comprise coupling a first frictional element to the first earpiece proximate the first loop to retain the first earpiece through the first loop. The first frictional element is slidably adjustable along the first earpiece to adjust a length of the eyewear restraint.

The method can comprise disposing a second earpiece of the pair of eyewear through a second loop of the second strap such that the second earpiece extends at least partially through the second loop. The method can comprise coupling a second frictional element to the second earpiece proximate the second loop to retain the second earpiece through the second loop. The second frictional element is slidably adjustable along the second earpiece to adjust a length of the eyewear restraint.

In one example there is provided a method of making an eyewear restraint. The method can comprise forming a first strap comprising a first adjustment end and a first eyewear-coupling end, with said first eyewear coupling end being coupleable to a first eyewear frame portion. The method can comprise forming a second strap comprising a second adjustment end and a second eyewear-coupling end, with said second eyewear coupling end being coupleable to a second eyewear frame portion. Thus, said first strap and said second strap are slidably engageable to one another to allow adjustment of a length of the restraint by moving at least one of the first adjustment end and the second adjustment end relative to the other one. The method can comprise forming a loop by securing a first strap edge to a second strap edge to form an attachment portion, wherein the attachment portion is substantially in-line with the first strap edge.

There has thus been outlined, rather broadly, general invention features so that the detailed description thereof that follows may be better understood, and so that the present contribution to the art may be better appreciated. Other invention features will become clearer from the following detailed description, taken with the accompanying drawings and claims.

BRIEF DESCRIPTION OF THE DRAWINGS

FIG. 1A is a perspective view of an adjustable eyewear restraint coupled to a pair of eyewear in accordance with one example;

FIG. 1B is a perspective view of an adjustable eyewear restraint coupled to a pair of eyewear in accordance with one example;

FIG. 4A shows inner and outer views of the adjustable eyewear restraint of FIG. 1B in an lengthened state in accordance with one example;

FIG. 4B shows inner and outer views of the adjustable eyewear restraint of FIG. 1B in a shortened state in accordance with one example;

FIG. 5A shows an inner view and a side view strap of an adjustable eyewear restraint in accordance with one example;

FIG. 5B shows an inner view and a side view of an adjustable eyewear restraint in accordance with one example;

FIG. 7A is a schematic outer view of a strap of an adjustable eyewear restraint in accordance with one example;

FIG. 7B is a schematic outer view of a loop formed from the strap of FIG. 7A in accordance with one example;

FIG. 8A is a schematic outer view of a frictional element of a strap of an adjustable eyewear restraint in accordance with one example;

FIG. 8B is a schematic outer view of an earpiece retained in the frictional element of FIG. 8A in accordance with one example; and FIG. 9 shows various views of a retainer device for coupling an eyewear restraint to an earpiece of an eyewear in accordance with one example.

Figure 2A:
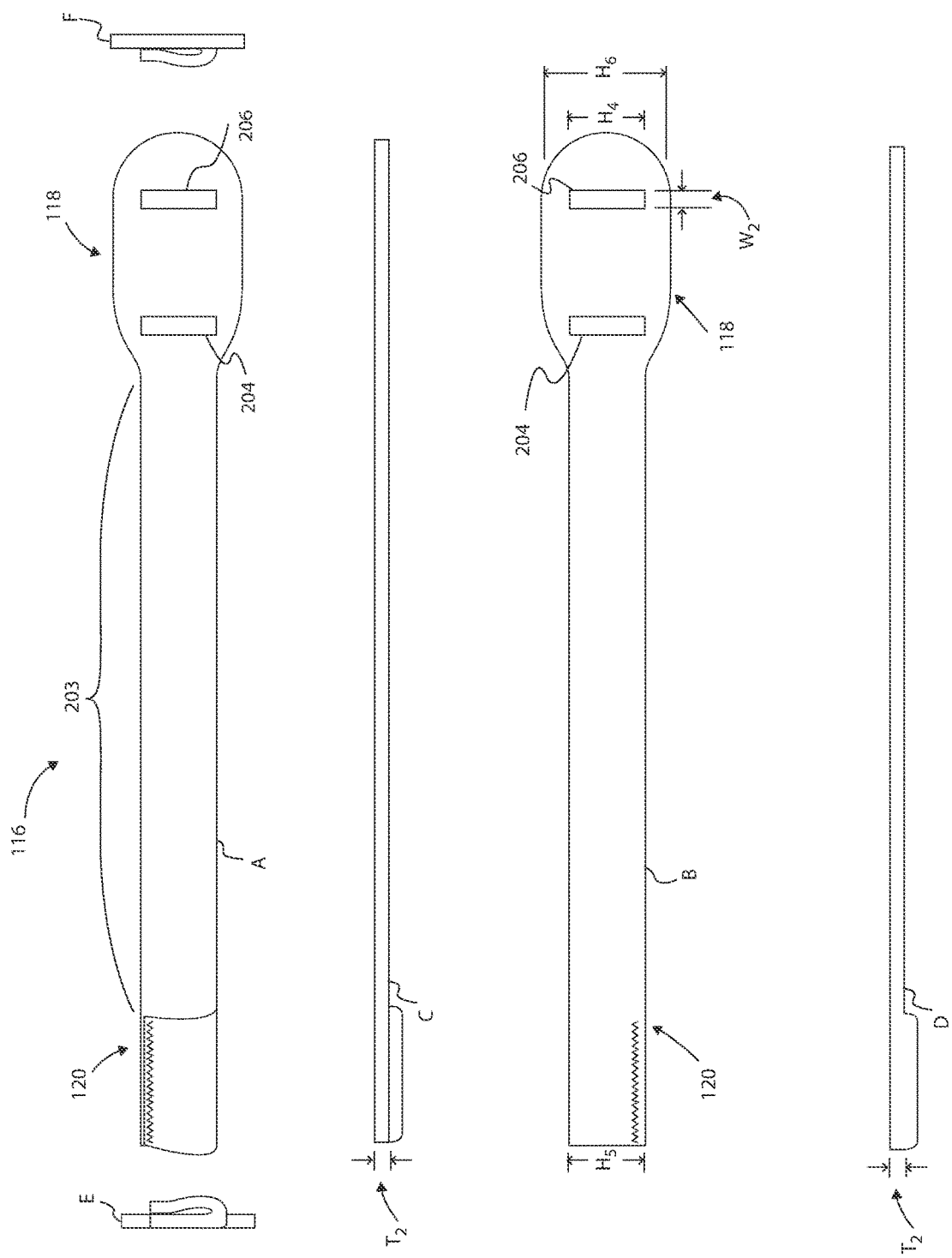
FIG. 2A shows various views of a strap of the restraint of FIG. 1B in accordance with one example.

These drawings are provided to illustrate various invention aspects and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" provide express support plural referents in the written description unless the context clearly dictates otherwise. Thus, for example, reference to "a material" includes reference to one or more of such materials and reference to "the subject" refers to one or more subjects.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

The term "coupled," as used herein, is defined as directly or indirectly connected. "Directly coupled" is defined as actual physical contact or attachment between two objects, structures, or items. "Indirectly coupled" means that two objects are connected by at least one intermediate object or structure. Objects, structures, or elements described herein as being "adjacent to" each other may be connected, in physical contact with each other, or in close proximity to each other, as appropriate for the context in which the phrase is used.

The terms "first," "second," "third," "fourth," and the like in the written description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation or use in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the written description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data, including dimensions, weight, density, etc., may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the written description, like "comprising" or "including," it is understood that direct support should be afforded also to "consisting essentially of" language as well as "consisting of" language as if stated explicitly and vice versa.

Adjustable Eyewear Restraints

An initial overview of technology embodiments is provided below and specific technology embodiments are then described in further detail. This initial summary is intended to aid readers in understanding the technology more quickly, but is not intended to identify key or essential features of the technology, nor is it intended to limit the scope of the claimed subject matter.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

FIG. 1A shows an adjustable eyewear restraint 100 coupled to a pair of eyewear 102 in accordance with one example, and FIG. 1B shows an adjustable eyewear restraint 104 coupled to a pair of eyewear 106 in accordance with one example.

Regarding FIG. 1A, the adjustable eyewear restraint 100 comprises a first strap 108 comprising a first adjustment end 110 and a first eyewear coupling end 112. The first eyewear-coupling end 112 can be coupled to a first eyewear frame portion 114, such as an earpiece 115 (or the eyewear-coupling end may be directly coupled to another portion of an eyewear frame, such as ski or scuba goggles, for instance). The adjustable eyewear restraint 100 comprises a second strap 116 comprising a second adjustment end 118 and a second eyewear-coupling end 120. The second eyewear-coupling end 120 can be coupled to a second eyewear frame portion 122, such as an earpiece 123 of the eyewear 102. As further described below, the first strap 108 and the second strap 116 are slidably engaged (or engageable) to one another to allow adjustment of a length of the restraint 100 by moving at least one of the first adjustment end 110 and the second adjustment end 120 relative to the other one (see e.g., FIGS. 3A-4B).

Similarly (but somewhat inversely), FIG. 1B shows the adjustable eyewear restraint 104 comprising a first strap 150 comprising a first adjustment end 152 and a first eyewear-coupling end 154. The first eyewear-coupling end 154 can be coupled to a first eyewear frame portion 156, such as an earpiece 158. The adjustable eyewear restraint 104 comprises a second strap 160 comprising a second adjustment end 162 and a second eyewear-coupling end 164. The second eyewear coupling end 164 can be coupled to a second eyewear frame portion 166, such as an earpiece 168 of the eyewear 106. As further described herein, the first strap 150 and the second strap 160 are slidably engaged (or engageable) to one another to allow adjustment of a length of the restraint 104 by moving at least one of the first adjustment end 152 and the second adjustment end 162 relative to the other one (see e.g., FIGS. 3A-4B).

FIG. 1B will not be discussed in as much detail as the configuration of FIG. 1A, but as can be appreciated from comparing the views of FIGS. 1A and 1B (and the following description), the restraint 104 of FIG. 1B has an inverse configuration to that of restraint 100 of FIG. 1A. Meaning that the straps are reversed, but effectively operate the same, and are similarly shaped and sized. Of further note, FIG. 1B is illustrated to show straps that are slightly larger and thicker than that of FIG. 1A, which is to illustrate that the straps of the restraint 104 can be comprise a relatively thicker positively buoyant material (e.g., neoprene) having a selected volume and density sufficient to impart positive buoyancy on the pair of eyewear when the restraint 104 and eyewear 106 are in fresh or salt water. For example, assume the pair of eyewear weigh at least 30 grams, then the restraint can be a selected type of material, an overall volume of material, and a density to impart a collective positive buoyancy to the restraint and the eyewear. Thus, if the restraint and eyewear are dropped into fresh or salt water, they will float for easy retrieval. This can also be true for the restraint 100 of FIG. 1A.

FIGS. 2A-4B show various views and configurations of the adjustable eyewear restraint 100 of FIG. 1A. Specifically, FIG. 2A shows the second strap 116 and FIG. 2B shows the first strap 108. FIG. 2A shows first side view (e.g. inside view) A, a second side view (e.g. outside view B), a top view C, a bottom view D, an eyewear-coupling end view E, and an adjustment end view F, of the second strap 116. Likewise, FIG. 2B shows a first side view (e.g. and inside view) view G, a second side view (e.g. an outside view) H, a top view I, a bottom view J, an eyewear-coupling end view K, and an adjustment end view L, of the first strap 108.

In one example, the first strap 108 comprises the adjustment end 110 that has a first opening 200 (such as a slot or other aperture) formed through the adjustment end 110. The first opening 200 can be vertically oriented relative to the horizontal length of the strap 108, and can have a height $H_1$ and a width $W_1$. The first strap 108 comprises a middle section 202 defined between the adjustment end 118 and the eyewear coupling end 112. The middle section 202 has a height $H_2$ and a thickness $T_1$, and the adjustment end 118 has a height $H_3$, which is sized larger than $H_1$ and sized to allow a wearer to grab a portion of the adjustment end 118. Similarly, the second strap 116 comprises the adjustment end 110 that includes a second opening 204 and a third opening 206, such as parallel slots, formed through the adjustment end 110. The second and third openings 204 and 206 each have a height $H_4$ and a width $W_2$, which may be the same or substantially the same dimensions as $H_1$ and $W_1$ of the first opening 200. The second strap 116 comprises a middle section 204 between the adjustment end 110 and the eyewear-coupling end 120. The middle section 204 has a height $H_5$ and a thickness $T_2$, and the adjustment end 110 has a height $H_6$.

The openings 200, 204, and/or 206 can be rectangular slots formed vertically as shown, or they can be straight openings or arced/non-linear openings, and can be slits, ellipses, or any other suitable configuration that can receive a middle section of either strap, as the case may be. In one embodiment, the openings do not have a closed perimeter, but rather can include an opening that reaches an edge of the strap to form a "U-shaped open slot" for example. Such an opening at the edge of the strap allows engagement of the other strap by sliding the strap through the open edge. This may be useful in cases where the adjustment ends are semi-rigid or rigid to provide sufficient structural support for an open slot to receive a middle section from an upper or lower area of the slot, for example.

Figure 2B:
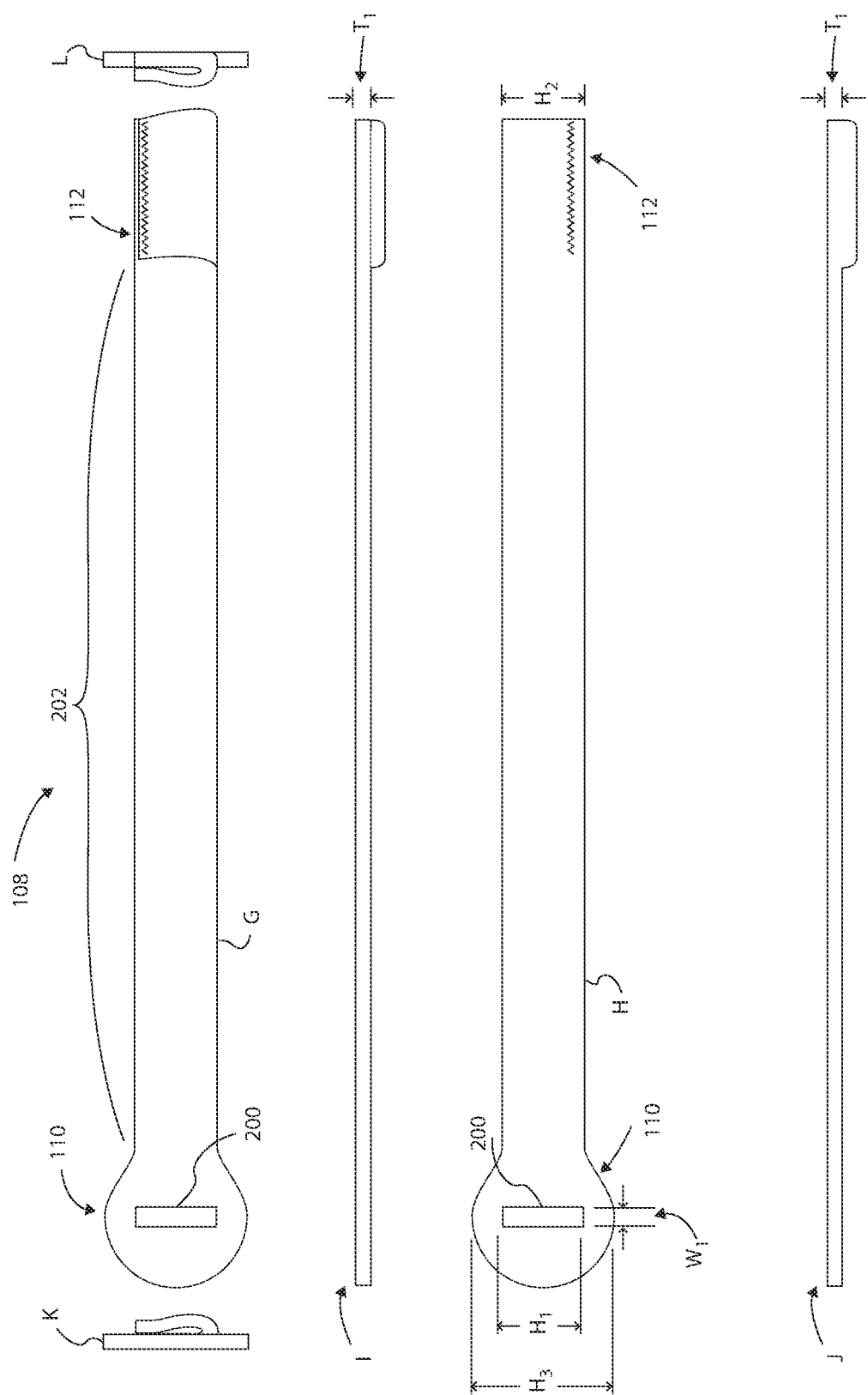
FIG. 2B shows various views of a strap of the restraint of FIG. 1B in accordance with one example.

As illustrated best on FIGS. 2A and 2B, the straps 108 and 116 are substantially planar along the length of the adjustment ends and the middle sections. This helps to overlay the straps on each other and flat against a wearer's head, which further contributes to the frictional force between the straps because surfaces of the middle sections can be slidably biased against each other to increase the frictional force between the straps.

Figure 3A:
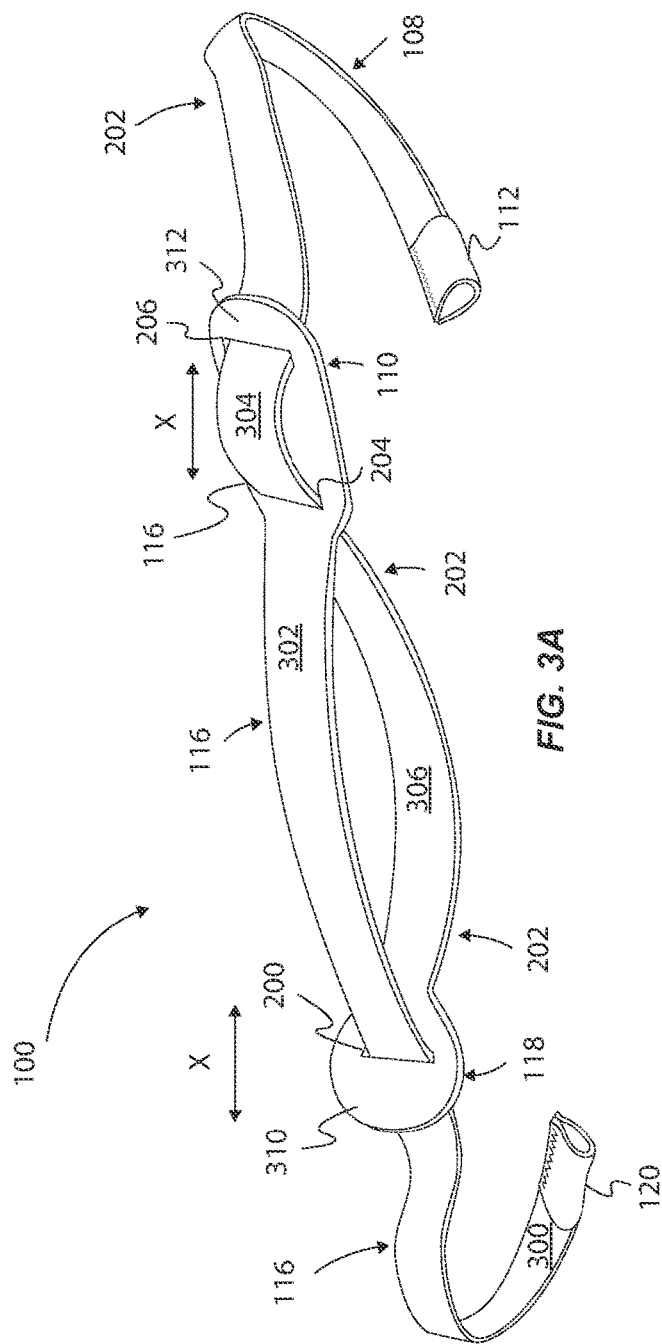
FIG. 3A is a perspective view of the adjustable eyewear restraint of FIG. 1B in accordance with one example.
Figure 3B:
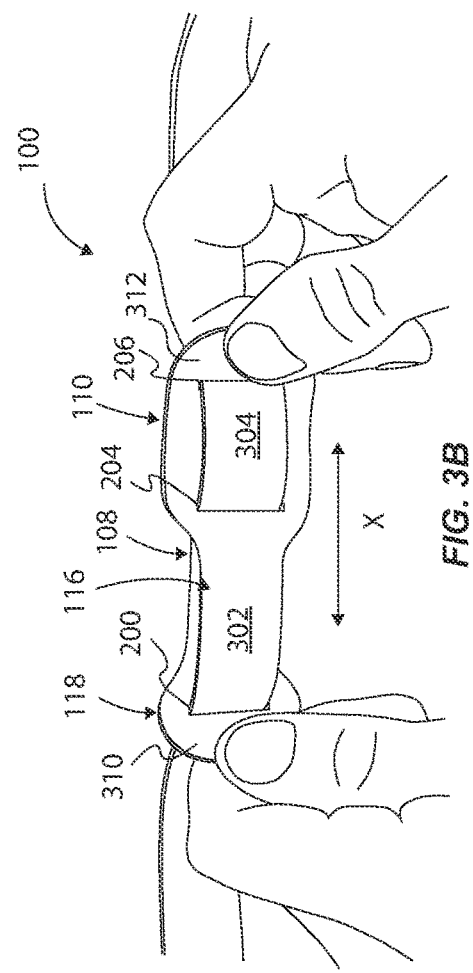
FIG. 3B illustrates adjustability of the adjustable eyewear restraint of FIG. 1B in accordance with one example.

As further illustrated on FIGS. 3A and 3B, a portion of the middle section 202 of the first strap 108 extends through the second opening 204 of the second strap 116 about an inner side 300 of the second strap 116. A portion of the middle section 202 of the first strap 108 further extends through the third opening 206 about an outer side 302 of the second strap 116, and through toward the inner side 300 of the first strap 108. Thus, a transition section 304 of the first strap 108 extends between the second and third openings 204 and 206. Similarly, the second strap 116 extends through the first opening 200 about an outer side 306 of the first strap 108. Accordingly, the first strap 108 is in an interwoven configuration with the second strap 116, as shown, through the second and third openings 204 and 206. Therefore, the straps 108 and 116 are slidably interwoven to each other about respective adjustment ends to form a substantially planar retainer configuration. This is best shown on FIGS. 1A and 1B where the retainers are collectively substantially flat (in an arc) when overlaying each other on a wearer's head. The openings of the adjustment ends need not be disposed through the adjustment ends. Rather, they could be disposed through an area of the middle section(s) of the straps.

Accordingly, the first and second straps 108 and 116 are slidably engaged to each other and movable relative to each other, bi-directional, as illustrated by arrows X on FIG. 3B when a wearer pulls the adjustment ends 110 and 118 toward each other or away from each other. In this way, the adjustment end 118 can have a pull tab 310 and the adjustment end 110 can have a pull tab 312. The pull tabs 310 and 312 can be sized and shaped, as shown, such that a wearer can grip each tab with a respective thumb and index finger, for example, when adjusting the restraint 100. Any shape, size, or configuration that facilitates or eases grasping by a user can be employed. Advantageously, the pull tabs 310 and 312 are each positioned on the same side, specifically on an outer side of the restraint 100 (e.g. outer, or side facing away from a user's head when the restraint is in use), so that the wearer can readily locate and pull the tabs as desired. In an alternative embodiment, the pull tabs can both be positioned on the other side of the straps (i.e. on the inner or side facing toward a users' head when the restraint is in use) however, and can have an additional finger engagement portion than as shown, for example, elongated or enlarged shapes (e.g. a flange) that allow a user to grasp the tabs above, or below the straps. In some embodiments, the tabs can be on opposite sides of the retainer with one tab on a side facing away from a user's head and the other tab on a side facing toward the user's head. Again, enlarged or flanged shapes can be used to aid a user's grasp on the tabs.

The openings 200, 204 and 206 are sized and shaped, and selected from a particular material, to provide a frictionally adjustable restraint 100 about a wearer's head. More specifically, middle section 202 is frictionally and slidably coupled to the second and third openings 204 and 206, and middle section 204 is frictionally and slidably coupled to the first opening 200. The straps 108 and 116 can be comprised of an elastomeric or highly elastomeric, material or fabric (e.g. neoprene) material having a known friction coefficient such that, when arranged as in FIG. 3A, a certain amount of pulling force (kinetic friction force) is required to overcome the (static) frictional force between the openings 202, 204 and the middle section 202 of the first strap 208. Alternatively, the straps can be made from a less elastomeric material (e.g. leather), which can impart frictional forces between the straps similarly as neoprene straps, or can include the use of an additional piece of friction-adding material. Furthermore, friction can be increased for less elastomeric materials by increasing the number of openings or slots through which the straps pass or are interwoven. In some embodiments, each strap can include between 1 and 5 lots or openings. In other embodiments, the number of openings on each strap can be different and thus allow both pull tabs 310 and 312 to be on the same side of the restraint. For example, one strap can have an even number of openings or slots while the other strap has an even number of openings or slots. In alternative embodiments, when the pull tabs 310 and 312 are on opposite sides of the restraint, the number of openings or slots in each strap can be the same, or can be both an even number or both an odd number.

Of note, the angle or direction at which each strap extends through a respective opening contributes to the frictional force (static and kinetic) existing between the straps and the opening(s) through which the strap(s) extends. For instance, as illustrated on FIG. 3A, the first strap 108 extends through the second opening 204 from a lower left direction such that the second opening 204 tends to pinch or bind the strap 208, thereby contributing to the friction between the straps when on a wearer's head.

In some examples, the force required to move or slide one of the adjustment ends relative to a strap can be 0.10 pounds, and up to 2.5 pounds (i.e., 0.20 pounds of collective force to move both adjustment ends, for instance). In some instances, such as with prescription glasses weighing only 15-20 grams, for instance, said force can be less than 0.10 pounds. In other instances with larger, heavier eyewear (e.g., 30 grams or more), said force for each adjustment end can be more than 0.10 pounds, and sometimes greater than 2.5 pounds of force to move an adjustment end. Thus, a particular restraint can be "tuned" for a particular application, such as selecting certain materials for straps, having certain sized openings and strap dimensions, etc.

In some examples, the opening 200 can have the height $H_1$ that is shorter than a height $H_5$ of the middle section 203 of the second strap 116. Likewise, width $W_1$ can be shorter than thickness $T_1$ of the first strap 108. Said another way, the area defined by the opening 200 can be smaller than a cross sectional area of the middle section 203 of the second strap 116. In this manner, because neoprene is compliant (and flexible), for example, the opening 200 can effectively "squeeze" or compress the second strap 116 to increase or optimize the frictional force between the straps to a desired frictional force (static and kinetic). The same holds true for the second and third openings 204 and 206 that receive the first strap 108. In other examples, the openings 200, 204, and/or 206 can have an area larger than a cross sectional area of respective middle sections extending through said opening(s), which can be advantageous in examples where the straps are comprised of a more rigid material than neoprene, such as woven fabric, leather, and the other similar materials (or in examples where the adjustment ends and/or openings are comprised of a rigid material, such as certain plastics, rubbers, etc.). In any event, the openings can be sized and shaped to impart a desired frictional force between the straps such that an attached pair of eyewear is restrained on a wearer's head, and such that the restraint 100 is only adjusted when desired by the wearer (i.e., by pulling on the adjustment end(s)).

In some examples, a particular neoprene strap (108 and 116, for example) can have a thickness (e.g., $T_1$ or $T_2$) of 0.5 mm up to 5.0 mm. As known, neoprene straps have a rubber core that is laminated with a polyester or nylon fabric. Therefore, such fabric coating (e.g., inner and outer sides of straps 108 and 116) will have a known and selectable coefficient of friction, and the rubber core (e.g., within an opening) will have a known and selectable coefficient of friction. Such coefficients are factors when determining the size of the openings, the thickness of the straps, etc.

In some examples, a variety of neoprene materials can be used to form the straps 108 and 116 (for example), such as F Foam, J Foam, K Foam, L Foam, and the like, and combinations thereof. In one example of the straps 108 and 116 being comprised of L Foam neoprene, such material has a density of approximately 0.17-0.21 g/cm$^3$ and a compression deflection of 0.28-0.38 kg/m$^3$. Accordingly, assuming each strap is 4 mm thick, 23 cm long, 19 mm tall at the middle section, and approximately 32 mm tall at the adjustment end section, an L Foam neoprene material would necessarily provide sufficient positive buoyancy to a pair of eyewear weighing approximately 30 grams or less, for instance. Moreover, an L Foam neoprene material with a nylon fabric coating would have sufficient friction between the straps about respective openings and strap surfaces to hold a pair of eyewear about a wearer's head.

FIG. 4A shows a first side (e.g. an inner side) view I and a second side (e.g. an outer side) view O of the restraint 100 in a loosened position L, and FIG. 4B shows first side (e.g. an inner side) view I and a second side (e.g. an outer side) view O of the restraint 100 in a tightened position T. This means that, on FIG. 4A, the adjustment ends 110 and 118 are positioned adjacent or proximate each other such that a length of the restraint 100 is at or near its longest possible configuration. Conversely, FIG. 4B shows the adjustment ends 110 and 118 farther away from each other than on FIG. 4A such that a length of the restraint 100 is at or near its shortest (e.g., worn tightest) possible configuration.

FIGS. 5A and 5B illustrate an example of removably attaching straps of a restraint. Each Figure shows an inner view I of a strap and a side view S of said strap. Specifically, a first strap 508 can have a similar shape and configuration as the first strap 108 of FIG. 2B. Accordingly, the first strap 508 can have an adjustment end 518 having a first opening 500, and a middle section 502 (only partially shown). And, a second strap 516 (FIG. 5B) can have a similar shape and configuration as the second strap 116 of FIG. 2A. Accordingly, the second strap 516 can have an adjustment end 510 having second opening 504 and a third opening 506, and a middle section 503 (only partially shown). Therefore, the first strap 508 can be slidably and frictionally engaged to the first opening 500, and the second strap 516 can be slidably and frictionally engaged to the second and third openings 504 and 506, as similarly shown on FIGS. 3A and 3B.

The first strap 508 can comprise a first male attachment 550 and a first plurality of female attachments 552 (e.g., holes through the strap). Likewise, the second strap 516 can comprise a second male attachment 554 and a second plurality of female attachments 556. The male attachments 550 and 554 can be posts with a flange that extends from an inner surface of respective adjustment ends 510 and 518. The male attachments 550 and 554 can be sized and shaped to frictionally fit or snap-fit through a selected female attachment of an opposing strap. For example, the first male attachment 550 can be interlocked to (e.g., removably coupled to) one of the second plurality of female attachments 556, which removably secures the first strap 508 to the second strap 516. In this way, a flange 558 of a post 560 of the male attachment 550 is disposed through a female attachment 552 on an opposing side of the strap 516 such that the flange 558 retains the adjustment end 518 to the strap 516. The male attachment 550 can then be removed by pulling on the adjustment end 518, for instance, and then coupled to a different female attachment 556 for adjusting a length of a restraint as desired. Likewise, the second male attachment 554 can be interlocked to (e.g., removably coupled to) one of the first plurality of female attachments 552, which removably secures the second strap 516 to the first strap 508. In some examples, the male and female attachments are comprised of a semi-rigid material, such as certain plastics and polymers, to ensure proper attachment between the male and female attachments.

Figure 6B:
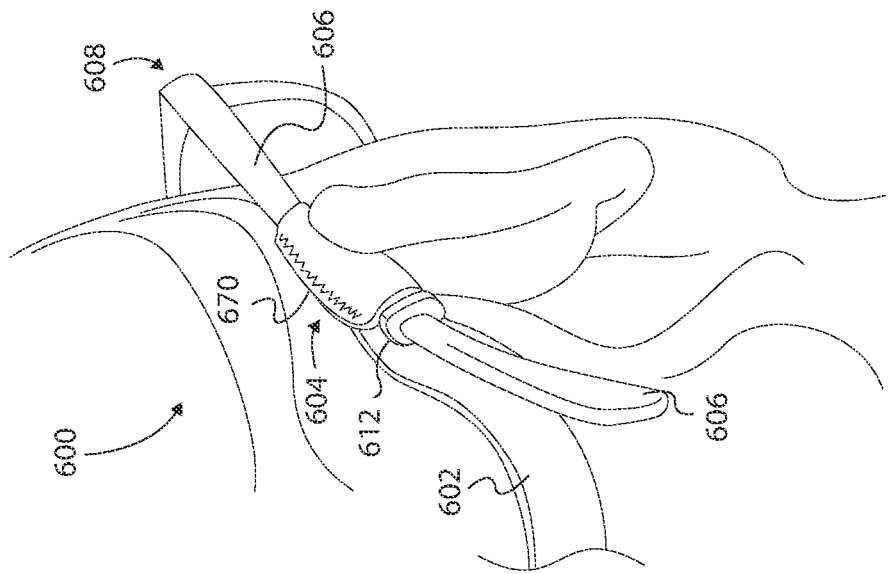
FIG. 6B is a perspective view of the adjustable eyewear restraint of FIG. 6A in accordance with one example.
Figure 6A:
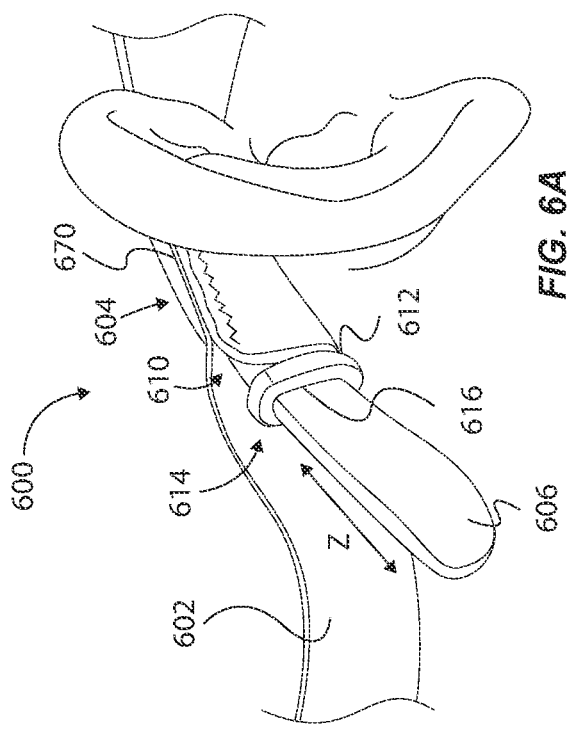
FIG. 6A is a perspective view of an adjustable eyewear restraint in accordance with one example.

FIGS. 6A and 6B illustrate an adjustable eyewear restraint system 600 according to one example. The system 600 can comprise a strap 602 having an eyewear-coupling end 604 slidably coupleable to an earpiece 606 of a pair of eyewear 608, such as described with reference to FIGS. 1A and 1B. The eyewear-coupling end 604 comprises a loop 610 size and shaped to allow a portion (e.g., an end) of the earpiece 606 to pass through the loop 610 (e.g., see loop 714 of FIG. 7B). In one example, a cross sectional area of the loop 610 is the same size or smaller than a cross sectional area of the earpiece 606, thus allowing the loop to frictionally (e.g. tightly) engage the earpiece 606. In this embodiment, the elastomeric material can be selected so as to exert a sufficient frictional force to retain the earpiece in the loop without further assistance. In some embodiments, the inner material of the loop can be a material with a coefficient of friction that further aids in retaining the eyepiece within the loop (e.g. channel, tube, etc.) and the length of the loop can further be used to add or reduce the frictional relationship between the loop and the earpiece. In some embodiments, the loop can have a larger than a cross sectional area of the earpiece 606 such that the loop 610 loosely fits around the earpiece 606. This allows for the loop 610 to easily engage a variety of sizes of earpieces without the requirement of substantial force during the engagement process. It also prevents the loop 610 from stretching out or failing due to exhaustion or fatigue in the material thus causing the friction fit to be reduced or lost. Thus, having the loop sized to be loose around an earpiece provides longevity of the loop 610 and reliability for repeated uses and/or with different sized earpieces.

In embodiments where the loop 610 is loosely fit around the earpiece 606, a frictional element 612 can be coupled to the earpiece 606 and positioned adjacent the loop 610 proximate an inner side 614 of the loop 610. The loop and frictional element can work cooperatively as a system for retaining the eyewear. In one example, the frictional element 612 is an O-ring having a perimeter body section with a cross sectional area larger than a cross sectional area of an opening of the loop 610 (FIGS. 6A and 6B). The frictional element 612 can have an aperture 616 sized and shaped sufficient to frictionally engage the earpiece 606 and retain the earpiece 606 within the loop 610, thereby preventing the loop 604 from sliding off of the earpiece 606. In one example, the frictional element 612 can comprise a compliant material that is frictionally and slidably coupled to the earpiece 606 for adjustment of the eyewear coupling end 604. This means that the frictional element 612 can be slidably moved by a wearer bi-directionally along the earpiece 606 (see arrows Z) such that the eyewear coupling end 604 is also slidably moved about the same direction and distance as the frictional element 612 along the earpiece 606. Such movement of the eyewear coupling end 604 can therefore adjust a length of the strap 602 of a restraint. Therefore, a pair of frictional elements such as 612 can be incorporated with the adjustable eyewear restraint 100 of FIG. 1A, which therefore provides an additional mechanism to adjust the straps about a wearer's head to a desired position and tightness, for instance. Any material, size, or shape that can provide sufficient friction to hold in place on an earpiece can be used.

Furthermore, dual-systems for adjusting an eyewear restraint are possible when a pair of frictional elements like 612 (or 662 of FIG. 6C) are incorporated with the adjustable straps of FIGS. 1A-6B, thereby combining two systems of adjustability. And, when the adjustable straps are pulled, as on FIG. 3B, the frictional elements of the present disclosure provide a counter-acting force against the pulling force of the wearer in order to retain the eyewear coupling ends to a pair of eyewear.

Figure 6C:
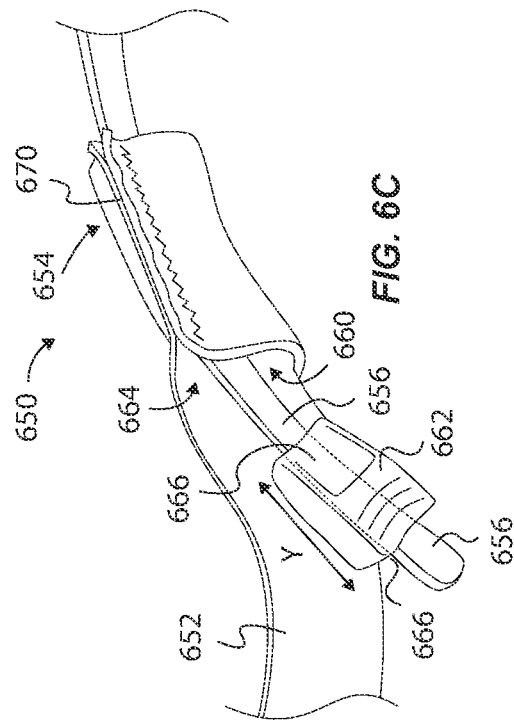
FIG. 6C is a perspective view of an adjustable eyewear restraint in accordance with one example.

FIG. 6C illustrates an adjustable eyewear restraint system 650 according to one example. The system 650 can comprise a strap 652 having an eyewear coupling end 654 slidably coupleable to an earpiece 656 of a pair of eyewear (e.g., 608), such as described with reference to FIGS. 1A and 1B. The eyewear coupling end 654 comprises a loop 660 (e.g., 714 of FIG. 7B) sized and shaped to allow a portion (e.g., an end) of the earpiece 656 to pass through the loop 660. In one example, a cross sectional area of the loop 660 is larger than a cross sectional area of the earpiece 656 such that the loop 660 loosely fits around the earpiece 656 (as with FIG. 6A). Accordingly, a frictional element 662 can coupled to the earpiece 656 and can be positioned adjacent the loop 660 proximate an inner side 664 of the loop 660. In one example, the frictional element 662 is a wedge (or other body) having a perimeter body section with a cross sectional area larger than a cross sectional area of an opening of the loop 660 to retain the earpiece 656 within the loop 654. The frictional element 662 can have an aperture 666 sized and shaped sufficient to frictionally engage the earpiece 656 and retain the earpiece 656 through the loop 660, thereby preventing the loop 654 from sliding off of the earpiece 656. The aperture 666 of the frictional element 662 can extend all the way through the frictional element 662 (as in FIG. 6C), or it can be a bore (not shown) that stops partially through the frictional element 662 to receive an end of the earpiece 656.

The aperture 666 can be sized to receive smaller earpieces (i.e., prescription frames) as can be seen when comparing FIG. 6A to FIG. 6C.

The frictional element 662 can comprise a compliant material and can be frictionally and slidably coupled to the earpiece 656 for adjustment of the eyewear coupling end 654. This means that the frictional element 662 can be slidably moved by a wearer bi-directionally along the earpiece 656 (see arrows Y) such that the eyewear coupling end 654 is also slidably moved in the same direction and distance as the frictional element 662. Such movement of the eyewear coupling end 654 can adjust a length of the strap 652. Therefore, a pair of frictional elements such as 662 can be incorporated with the adjustable eyewear restraint 100 of FIG. 1A, which therefore provides an additional mechanism to adjust the straps about a wearer's head to a desired position and tightness, for instance.

Notably, regarding FIG. 6A-6C, the eyewear coupling ends 604 and 654 each include an attachment portion 670 about which edges of the straps are attached together (e.g., sewn), as will be further discussed below. As shown, the attachment portion 670 is position in an upwardly facing manner relative to the earpiece and the wearer's standing position. This is advantageous over existing restraint systems because the attachment portion 670 does not contact the wearer's head (e.g., scalp and ear), which reduces or eliminates chaffing or skin irritation as compared to restraints that have different configurations where an attachment area contacts the wearer, as further discussed herein. In some embodiments that employ such eyewear coupling ends, the retainer can be either adjustable as described herein, or non-adjustable, for example, a single piece of material.

FIGS. 7A and 7B illustrate an eyewear-coupling end 700 and method of making the eyewear coupling end 700 (such as the eyewear coupling ends shown and discussed in FIGS. 1A-6C). Here, the eyewear-coupling end 700 is formed from a strap 702 of an eyewear restraint. The strap 702 has a first edge 704 and an opposing second edge 706, which may be substantially parallel to each other. The first edge 704 may extend along a distance of a length of the strap 702, such as on FIGS. 2A and 2B. The second edge 706 is shorter than the first edge 704. As shown on FIG. 7A (in a pre-completed configuration) the strap 702 is cut and shaped like a "key" such that the strap 702 has an elongated middle section 708 that has a consistent length and width and that is terminated proximate the location of the second edge 706. In other words, the second edge 706 can be positioned on a flange portion 710 at an end of the strap 702. The flange portion 710 is formed downwardly and substantially perpendicular from a length of the middle section 708 of the strap 702 (but it can be formed at other angles and/or curved edges).

Once the strap 702 is formed as shown on FIG. 7A, the flange portion 710 is rotated upwardly toward the first edge 704 (as shown by the arrow M) such that the first edge 704 and the second edge 706 are in-line and adjacent each other, thereby having proximately a common collective edge region. The first and second edges 704 and 706 can then be attached to each other to form an attachment portion 712 (such as 670 of FIGS. 6A-6C). Accordingly, a loop 714 is thereby formed having an outer opening 716 and an inner opening 718, which may have a substantially uniform or consistent tubular shape that is flexible and compliant, for instance. The outer opening 716 can receive an earpiece (e.g., FIG. 6A), and the inner opening 718 can allow the earpiece to pass through.

Therefore, the attachment portion 712 is configured such that the first edge 704 (e.g., upper edge) and the second edge 706 (e.g., lower edge) are attached together substantially in-line with the first edge 704, as shown on FIG. 7B. The resulting configuration provides an attachment portion 712 that is upwardly facing relative to an earpiece when on a wearer. The attachment portion 712 secures the first edge 704 to the second edge 706 by at least one of stitches, adhesive, fasteners (e.g., plastic crimps), liquid plastic (e.g., using UV rays to adhere), and combinations thereof. FIG. 7B shows fabric stitches 718 that attach the edges 702 and 706 together. It will be appreciated from the views that only a section of the first edge 702 is attached to the second edge 706.

As shown, the attachment portion 712 has a predetermined length that is approximately a length of the second edge 706, which can be between approximately ⅛ inch and ¾ inch. This is advantageous because existing systems can have loops that are 1 inch or longer, which can cause skin irritation or discomfort. The loop 714 can be sized and shaped to frictionally receive and retain an earpiece, or it can be sized and shaped to loosely receive an earpiece.

Although edge 704 is shown substantially linear, it can have a non-linear or flange portion extending upwardly proximate where it would be attached to the second edge 706 (e.g., FIG. 7A could show a somewhat "T" shape configuration).

FIGS. 8A and 8B illustrate an example of an adjustable eyewear restraint system 800. The adjustable eyewear restraint system 800 can comprise a strap 802 having an eyewear-coupling end 804 with a loop 806 to receive an earpiece 808, as similarly described herein. A frictional element 810 can be coupled to the strap 802 adjacent the loop 806 (e.g., on an inner side of the loop as shown). Here, the frictional element 810 is a frictional panel having a pair of openings 812 and 814. The frictional element 810 can be attached to the strap 802 by a pair of opposing stitches 816 and 818, or it can be attached by other devices, such as adhesive. As illustrated on FIG. 8B, a tip portion 820 of the earpiece 808 extends through opening 814 and through opening 812 in an interwoven manner such that a middle portion 822 of the frictional element 810 is exposed and assists to retain or pinch the earpiece 808 against the strap 802. The openings 812 and 814 can be slits or slots (or other apertures) that are sized and shaped to receive an earpiece while imparting friction between the strap 802, the frictional element 810, and the earpiece 808 to prevent the earpiece 808 from falling out on its own. The frictional element 810, therefore, is configured to retain the earpiece 808, but also allow the earpiece 808 to be inserted and removed with relative ease by a wearer. For instance, 0.5 pounds of force may be used to insert and removed the earpiece 808 about the frictional element 810. Here, the openings 812 and 814 are vertical slits relative to an elongated length of the strap 802, but the openings can be formed at different angles, arcs, and other configurations that can impart frictional force between the strap and the earpiece. In one example, slits or other openings can be formed directly through the strap 802 itself to receive and retain an earpiece.

FIG. 9 shows various views of an example frictional element 900 that can be removably coupled to an earpiece and to a loop of a strap to retain the earpiece to the strap. Here, the frictional element 900 comprises an earpiece retainer 902. Thus, FIG. 9 shows a side view S, a front view F, and a rear view R of the earpiece retainer 902. The earpiece retainer 902 can comprise a first end 904 and a second end 906. The first end 904 can be positioned through a loop 907 of a strap 909 (both 907 and 909 are illustrated in dashed lines), such at the loop and strap of FIG. 7B. The first end 904 can have an opening 908 sized and shaped to removably attach the earpiece retainer 902 to the earpiece. In this way, the earpiece retainer 902 can be comprised of a compliant material, such as certain plastics, rubbers, and polymers, which allows the opening 908 to expand slightly for a friction fit to an earpiece. The second end 906 can be positioned at least partially within the loop 907 and can have an enlarged interfacing portion 910 that frictionally couples the earpiece retainer 902 within the loop 907. In this manner, the enlarged interfacing portion 910 can be an outwardly tapered portion that has a cross sectional area larger than a cross sectional area of the loop 907 so that the earpiece retainer 902 cannot be removed through the loop to the right side (of the page) toward a pair of eyewear, but that it can only be removed to the left side away from pair of eyewear when removing the earpiece retainer 902 from an earpiece. This configuration retains an earpiece to the strap 909. The eyewear retainer 902 can have vertical ribs 912 that are frictionally engaged to an inner surface of the loop 907 to assist with retaining the retainer and attached earpiece to the loop and the strap. In practice, the earpiece retainer 902 is first inserted into the loop from an inner or left side of the loop 907 (as in FIG. 9), and then an earpiece of eyewear can be inserted through a right opening of the loop 907, and then the earpiece can be frictionally fit into the opening 908 of the eyewear retainer 902. These steps can be reversed for removal of the earpiece from the retainer 902.

In one example there is provided a method of adjusting a length of an eyewear restraint, such as shown and discussed regarding FIGS. 1A-9. The method can comprise pulling a first adjustment end 118 of a first strap 108 away from a second adjustment end 110 of a second strap 116 to shorten a length of the restraint 100 (or 104) to tightening an eyewear restraint about a wearer's head when coupled to a pair of eyewear (see e.g., FIG. 1). The first strap can be slidably and frictionally engaged to the second strap, as discussed specifically regarding FIGS. 3A and 3B. The method can comprise pulling the first and second adjustment ends towards each other to lengthen a length of the restraint to loosening the restraint about the wearer's head. The method can comprise disposing a first earpiece of the pair of eyewear through a first loop of the first strap such that the first earpiece extends at least partially through the first loop. The method can comprise coupling a first frictional element (e.g., 612, 662, 810, or 902) to the first earpiece proximate the first loop to retain the first earpiece through the first loop (e.g., see the discussion of FIGS. 6A-9). The first frictional element can be slidably adjustable along the first earpiece to adjust a length of the eyewear restraint. Likewise, the method can comprise similar operations to couple a second frictional element to an opposing earpiece of a pair of eyewear.

In one example there is provided a method of making an eyewear restraint, such as the adjustable eyewear restraints discussed regarding FIGS. 1A-7B. The method can comprise forming a first strap 108 comprising a first adjustment end 118 and a first eyewear-coupling end 112. Said first eyewear coupling end can be coupleable to a first eyewear frame portion (e.g., FIG. 6A). The method can comprise forming a second strap 116 comprising a second adjustment end 110 and a second eyewear-coupling end 120. Said second eyewear coupling end can be coupleable to a second eyewear frame portion (e.g., FIG. 6A). Thus, said first strap and said second strap are slidably engageable to one another to allow adjustment of a length of the restraint by moving at least one of the first adjustment end and the second adjustment end relative to the other one, such as described in greater detail regarding FIGS. 3A and 3B. The method can comprise forming a loop (e.g., 714 of FIG. 7B) by securing a first strap edge to a second strap edge to form an attachment portion, wherein the attachment portion is substantially in-line with the first strap edge, as further described in greater detail regarding FIGS. 7A and 7B.

The first and second straps discussed herein can be made of the same material or different materials. In one aspect, they can be made of the same material. In another aspect, they can be made of different materials. The straps can be made of a number of suitable materials. In one embodiment the materials can be flexible materials. In another embodiment they can be elastomeric materials. Non-limiting examples of materials that can be used to make the straps can include neoprene, neogreen, lycra, thermocline, silicone rubber, polyesters, polyamides, polypropylenes, cotton, silk, wool, leather, the like, and combinations thereof.

The adjustable eyewear restraints discussed herein can be adapted to engage a variety of eyewear devices. Non-limiting examples of eyewear can include prescription eyewear, non-prescription eyewear, safety or protective eyewear, swimming eyewear, magnification eyewear, electronic-display eyewear, and the like. In some aspects, the adjustable eyewear restraint can be universal or nearly universal and a single device can be capable of engaging and being used with nearly any type, size, or shape of eyewear.

Further, a variety of anchoring mechanisms can be used in the current technology. Non-limiting examples can include friction-fit mechanisms (such as 130a, 130b), closeable loops, cinches, tying mechanisms, snaps, buckles, Velcro, magnets, adhesive, and the like. Accordingly, the anchoring mechanisms can be adapted to temporarily or permanently attach the adjustable eyewear restraint to the intended eyewear. In one embodiment, the anchoring mechanism may simply be a tube that is made from the material of the restraint. When flexible elastomeric material is used for the restraint, the attachment ends may be created by simply folding the strap lengthwise and stitching it together to create a tube. The tube can then be engaged with an earpiece of an eyewear by sliding the tube lengthwise over the end of the earpiece.

The apertures can have any suitable size or geometry. In one aspect, the apertures are adapted to engage the interlocking straps with a degree of friction that provides a secure adjustment of the adjustable eyewear restraint. Accordingly, the adjustable eyewear restraint can be adjusted (i.e. tightened or loosened) by applying a sufficient amount of force to overcome the degree of friction between the interconnecting straps and their respective apertures. Further, the first strap can engage the pair of second apertures in the second strap with a first degree of friction and the second strap can engage the first aperture in the first strap with a second degree of friction. At least one of the first degree of friction, the second degree of friction, or the additive friction between these two interconnecting straps via the respective apertures can be sufficient to secure the eyewear in a desired/intended position on a user. The first degree of friction can be the same as, greater than, or less than the second degree of friction. The degree of friction can be adjusted based on the size and geometry of the apertures in the respective straps or bands, the size and geometry of the respective straps or bands, and/or the materials selected for the respective straps or bands.

What is claimed is:
1. An adjustable eyewear restraint, comprising:
a first strap comprising a first adjustment end and a first eyewear coupling end, said first eyewear coupling end being coupleable to a first eyewear frame portion; and
a second strap comprising a second adjustment end and a second eyewear coupling end, said second eyewear coupling end being coupleable to a second eyewear frame portion;
said first strap and said second strap being slidably engageable to one another to allow adjustment of a length of the restraint by moving at least one of the first adjustment end and the second adjustment end relative to the other one,
wherein the first strap comprises a first male attachment and a first plurality of female attachments, and wherein the second strap comprises a second male attachment and a second plurality of female attachments, wherein one of the first plurality of female attachments is selectively interlockable to the second male attachment, and one of the second plurality of second female attachments is selectively interlockable to the first male attachment.

2. The adjustable eyewear restraint of claim 1, wherein the first adjustment end of the first strap includes a first opening slidably frictionally engageable to the second strap, and wherein the second adjustment end of the second strap includes a second opening and a third opening, each of the second and third openings slidabley frictionally engageable to the first strap.

3. The adjustable eyewear restraint of claim 2, wherein each opening is sized and shaped to provide sufficient frictional force, between the opening and the respective strap slidably engageable there through, to retain the straps to each other about a wearer's head.

4. The adjustable eyewear restraint of claim 3, wherein each opening has a cross sectional area smaller than a cross section area of the respective strap slidably engageable through the respective opening.

5. The adjustable eyewear restraint of claim 1, wherein each adjustment end comprises a pull tab positioned on the same side of the retainer when the straps are slidably engaged to each other.

6. The adjustable eyewear restraint of claim 1, wherein each strap comprises at least one of neoprene, neogreen, lycra, thermocline, silicone rubber, polyesters, polyamides, polypropylenes, cotton, silk, wool, leather, and combinations thereof.

7. The adjustable eyewear restraint of claim 1, wherein the straps are slidably engaged to each other such that a length of the retainer is shortened when the adjustment ends are pulled away from each other, and such that a length of the retainer is lengthened when the adjustment ends are pulled toward each other.

8. The adjustable eyewear restraint of claim 1, wherein the straps are slidably interwoven to each other about respective adjustment ends to form a substantially planar retainer configuration.

9. The adjustable eyewear restraint of claim 1, wherein each strap comprises a first edge and an opposing second edge attached together, proximate respective eyewear coupling ends, to form a loop that receives a respective earpiece, wherein the edges are attached to form an attachment portion substantially in-line with the first edge.

10. The adjustable eyewear restraint of claim 1, further comprising:
a frictional element coupled to an earpiece at each of the first and second eyewear coupling ends.

11. The eyewear restraint system of claim 10, wherein the frictional element comprises a compliant material and has an aperture sized and shaped to receive the earpiece such that the frictional element is frictionally and slidably coupleable to the earpiece for adjustment of the eyewear coupling end.

12. The eyewear restraint system of claim 10, wherein the compliant material comprises a rubber material.

* * * * *